United States Patent [19]

Tsuchioka et al.

[11] Patent Number: 5,912,361
[45] Date of Patent: Jun. 15, 1999

[54] PROCESS FOR PRODUCING D-GLUCURONOLACTONE

[75] Inventors: Toshiki Tsuchioka; Tadashi Yamaguchi, both of Hiroshima-ken; Kunihiko Yuuen; Hiroto Chaen, both of Okayama-ken, all of Japan

[73] Assignees: Chugoku Kayaku Kabushiki Kaisha, Hiroshima-ken; Hayashibara Biochemical Laboratories, Inc., Okayama-ken, both of Japan

[21] Appl. No.: 09/037,089

[22] Filed: Mar. 9, 1998

[30] Foreign Application Priority Data

Mar. 10, 1997 [JP] Japan .................................. 9-055075

[51] Int. Cl.⁶ .................................................. C07H 7/033
[52] U.S. Cl. ........................ 549/311; 549/263; 549/295; 549/297; 435/41; 536/123.13
[58] Field of Search ................................... 549/295, 297, 549/311

[56] References Cited

FOREIGN PATENT DOCUMENTS

| | | |
|---|---|---|
| 0606753 | 7/1994 | European Pat. Off. . |
| 0628630 | 12/1994 | European Pat. Off. . |
| 0636693 | 2/1995 | European Pat. Off. . |
| 0671470 | 9/1995 | European Pat. Off. . |
| 0674005 | 9/1995 | European Pat. Off. . |
| 0688867 | 12/1995 | European Pat. Off. . |
| 0695804 | 2/1996 | European Pat. Off. . |
| 0704531 | 5/1996 | European Pat. Off. . |
| 670929 | 4/1950 | United Kingdom . |
| 727471 | 10/1951 | United Kingdom . |

OTHER PUBLICATIONS

Heyns, K., et al., "Selective Catalytic Oxidations of Carbohydrate," *Methods in Carbohydrate Chemistry* 6:342–347 (1972).

*Primary Examiner*—Jose' G. Dees
*Assistant Examiner*—Sabiha N. Qazi
*Attorney, Agent, or Firm*—Browdy and Neimark

[57] ABSTRACT

Trehalose is oxidized to give oxidized trehalose which then is hydrolyzed to produce D-glucuronolactone which is thereafter recovered to realize high-yield and low-cost production of D-glucuronolactone.

18 Claims, No Drawings

PROCESS FOR PRODUCING D-GLUCURONOLACTONE

BACKGROUND OF THE INVENTION

This invention relates to a process for producing D-glucuronolactone, more specifically, to a process for producing D-glucuronolactone by oxidizing trehalose and then hydrolyzing the oxidized trehalose.

Various processes are known be capable of producing D-glucuronolactone and many patent applications have been filed in the art. According to an already commercialized process, starch is oxidized with nitric acid and subsequently hydrolyzed to yield D-glucuronolactone. This method has the disadvantage that nitrogen monoxide having no oxidizing power foams in the process of production to interfere with the progress of a homogeneous oxidizing reaction and eventually lower the yield of D-glucuronolactone. In addition, the foaming nitrogen monoxide causes a cubic expansion of the reaction mixture and hence requires a reactor of an increased capacity. Other methods for producing D-glucuronolactone are described In Japanese Patent Publicaiton Nos. 25958/1967 and 5882/1968. These methods have solved the problem of foaming nitrogen monoxide but, on the other hand, no improvement has been made in the yield of D-glucuronolactone which is only about 10–15%.

Japanese Patent Publication No. 7325/1969 discloses a method of producing D-glucuronolactone by the steps of protecting glucose in C-1 position, oxidizing its C-position and subsequently hydrolyzing (deprotecting) the oxidizied glucose. However, the yield of D-glucuronolactone that can be produced by this method is still low (ca. 10–20%) and, in addition, the overall production process is complicated.

DISCLOSURE OF INVENTION

The present invention has been accomplished under these circumstances and aims at providing a process for producing D-glucuronolactone which gives high yield and which can be easily implemented on an industrial scale.

This object of the invention can be attained by a process for producing D-glucuronolactone comprising the steps of oxidizing trehalose, then hydrolyzing the oxidized trehalose to form D-glucuronolactone and recovering the same. The sequence of reactions that take place in the process of the invention for producing D-glucuronolactone is indicated below by Scheme 1 (provided that the first reaction starts with α, α-trehalose):

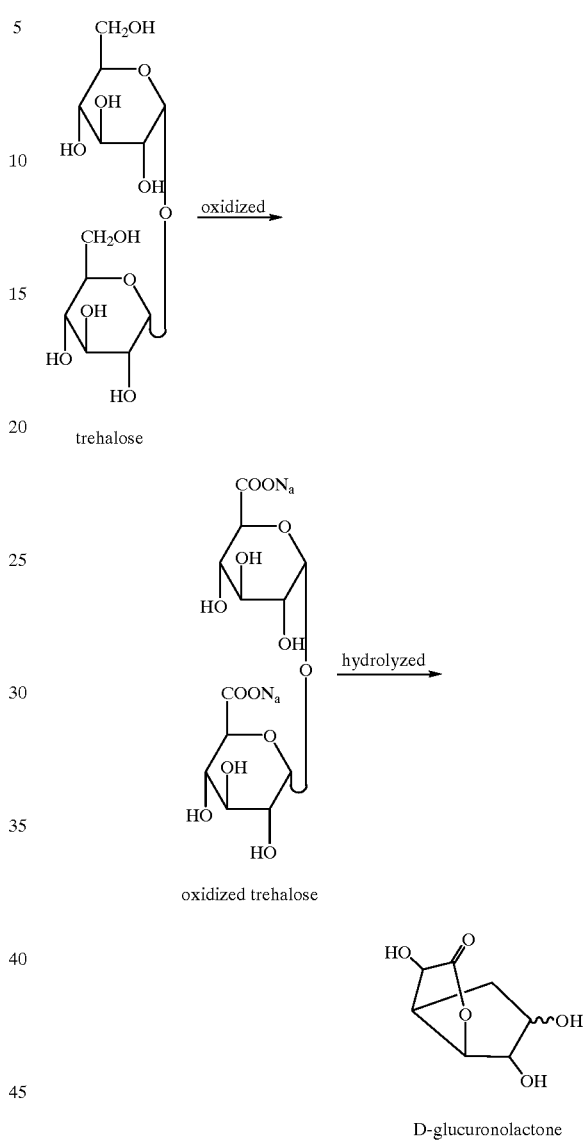

Scheme 1

BEST MODE FOR CARRYING OUT THE INVENTION

Trehalose (chemical formula=$C_{12}H_{22}O_{11}$; molecular weight=342.30) has long been known as a nonreducing disaccharide comprising D-glucose as a constituent sugar and depending on the mode of glucoside bonding, in three trehalose isomers exist, α, α-trehalose, α, β-trehalose and β, β-trehalose. The source and origin of the trehalose to be used in the invention are not limited in any particular way. Thus, the applicable trehalose may be an extract from bacteria, fungi, algae or insects or it may be obtained from maltose by the action of a complex enzyme system consisting of maltose phosphorylase and trehalose phosphorylase; alaternatively, maltose may be directly converted to trehalose with a maltose-trehalose converting enzyme, or a partial hydrolyzate of starch may be saccharified enzymatically. From the viewpoint of economy which requires producing D-glucurolactone of high quality at low cost, the trehalose produced by either the third or fourth method may be purified by a suitable method to produce trehalose of a higher purity and this is desirably used as the starting trehalose.

A preferred method of producing trehalose may proceed as follows. Starch is gelatinized and liquefied with an acid and/or α-amylase to produce a partial hydrolyzate of reducing starch comprising a malto-oligosaccharide in which the degree of polymerization of glucose is 3 or more, as exemplified by maltotriose, maltotetrose, maltopentose, and maltohexose; then the nonreducing saccharide generating enzyme disclosed in Japanese Patent Public Disclosure Nos. 143876/1995, 322883/1985, 66188/1996 and 84588/1996 is allowed to act on the starch hydrolyzate to convert it to a nonreducing saccharide having a terminal trehalose structure; subsequently, the trehalose liberating enzyme disclosed in Japanese Patent Disclosure Nos. 298880/1995, 213283/1995 and 66187/1996 and in the specification of Japanese Patent Application No. 189760/1995 is allowed to act on the resulting nonreducing saccharide so that trehalose is liberated from the latter. The nonreducing saccharide generating enzyme and the trehalose liberating enzyme may be allowed to act, either simultaneously or consecutively, on the nonreducing saccharide. The trehalose content of the product is further enhanced by using the two enzymes in combination with a starch debranching enzyme such as isoamylase or pullulanase. In order to effect direct conversion of maltose to trehalose, the maltose-trehalose converting enzyme disclosed in Japanese Patent Public Disclosure Non. 170977/1995, 263/1996, the specification of Japanese Patent Application No. 187901/1994 and Japanese Patent Public Disclosure No, 149980/1996 may be allowed to act on either maltose or a sugar composition containing maltose. If trehalose of a higher purity is required, the product of the above-described process may be subjected to column chromatography using a salt-form strong cationic exchange-resin in a fixed bed, a moving bed or a pseudo-moving bed so as to recover fractions of high trehalose content. The thus obtained product and fractions contain at least 70% of trehalose in the solids and are suitable for use as a raw material for the production of D-glucuronolactone.

To be oxidized, trehalose is dissolved in a suitable solvent, for example, at least one solvent selected from among water and straight-chain or branched lower alcohols such as methanol, ethanol, butanol and isopropyl alcohol and, thereafter, at least one known oxidizer selected from among inorganic nitrogen compounds such as nitric acid, nitrous acid and salts thereof, metal compounds such as manganese, chromium and lead compounds, halogens, inorganic halogen compounds, oxygen species such as air, oxygen and ozone, peroxides such as peroxonic acid, and organic compounds such as nitrobenzene, is added to oxidize the trehalose. Trehalose oxidation can advantageously be performed in the presence of an oxidizing catalyst such as platinum oxide, platinum on carbon, vanadium oxide or palladium on carbon, which are used to accelerate the oxidizing reaction. Trehalose can also be oxidized by electrooxidation or microbial oxidative fermentation. From an industrial viewpoint, namely, if the ease of handling and the yield of oxidized trehalose are taken into account, water can advantageously be used as the solvent, oxygen, ozone or air as the oxidizer, and platinum oxide or platinum on carbon as the oxidizing catalyst.

The oxidation reaction temperature should be high enough to allow for the progress of the reaction but insufficient to decompose trehalose, oxidized trehalose and D-glucuronolactone; typically, the oxidation reaction temperature is selected from the range of ca. 0–200° C., preferably ca. about 20–150° C., more preferably ca. 40–130° C., most preferably ca. 60–100° C. The time of oxidation reaction depends on the oxidizer used and the temperature and it is typically in the range of ca. 1–150 h, preferably ca. 5–80 h, more preferably ca. 10–30 h.

The oxidation reaction is preferably performed with pH adjustment, which is effectively done with pH typically in the range of 5–10, preferably 6–9, more preferably 7–8. Any bases that will not interfere with the reaction may be used for pH adjustment. Examples that may be used include sodium hydroxide, potassium hydroxide, calcium hydroxide, sodium carbonate, potassium carbonate, calcium carbonate, sodium hydrogendcarbonate, potassium hydrogencarbonate, magnesium hydroxide, ferrous hydroxide, ammonia, and alkylamines (e.g. trimethylamine, triehylamine, dimethylamine, diethylamine, monomethylamine, monoethylamine and so forth).

From an industrial viewpoint, sodium hydroxide, potassium hydroxide, calcium hydroxide, sodium carbonate, potassium carbonate, calcium carbonate, sodium hydrogencarbonate and potassium hydrogencarbonate are preferably used.

According to the oxidation reaction just described above, oxidized trehalose can be produced in high yields of at least 95% relative to the trehalose used as the raw material.

Hydrolysis of the oxidized trehalose can be easily accomplished by reacting it with one or more hydrolyzers selected from among acids such as hydrochloric acid, sulfuric acid, nitric acid, phosphoric acid and tosic acid in one or more solvents selected from among water and straight-chain or branched lower alcohols such as methanol, ethanol, butanol and ispropyl alcohol. Other methods of hydrolysis include the use of hydrolases. The temperature during hydrolysis which depends on the hydrolase used is selected from the range of ca. 0–200° C., preferably ca. 20–150° C., more preferably ca. 40–130° C., most preferably ca. 60–100° C. The time of hydrolysis is typically selected from the range of ca. 1–150 h, preferably ca. 5–80 h, more preferably ca. 5–10 h. Depending on their type, hydrolases are geverally allowed to act for ca. 1–150 h, preferably ca. 5–100 h, more preferably ca. 10–48 h. The thus obtained reaction product which contains D-glucuronolatone can typically be used as such after the unreacted reagents and/or the solvents are separated by filtration, extraction, solid-liquid separation, fractional precipitation, dialysis distillation, and so forth. If D-glucuronolactone of higher purity is required, techniques commonly used in the art for purifying sugars or sugar derivatives may be applied as exemplified by thin-layer chromatography, column chromatography, ion-exchange chromatography, gas chromatography, distillation and crystallization; these purifying techniques may be applied in combination as required. It should be noted that trehalose provides eight reactive radicals in a typical substitution reaction in which a nonionomeric hydroxyl group is a main player. This means that depending on the reaction conditions, a composition can be produced which contains not only D-glucuronolactone but also varying proportions of trehalose derivatives. Such a composition can typcially be used as such but, if necessary, one or more of the purifying techniques mentioned above may be applied prior to use in order to isolate the D-glucuronolactone only.

The above-described sequence of reactions enables D-glucuronolactone to be produced in yields of ca. 30–40% or even higher relative to trehalose used as the raw material. These values are twice to four times or even higher than have been achieved by the prior art.

The D-glucuronolactone produced by the process of the invention has a purity equal to or higher than that of the D-glucuronolactone produced by conventional known methods and, hence, it parallels the conventional version in that in various fields including the food, cosmetic and pharmaceutical industries, it finds extensive use as a substance having a conjugated poison removing or diminishing action, a hepatic function enhancing action, a fatigue lessening effect and an anti-rheumatic action. Examples of the present invention will now be described in detail.

EXAMPLES

Example 1: Production of D-glucuronolactone

Example 1-1: Preparation of Oxidized Trehalose

Three hundred grams (793 mmol) of α,α-trehalose, 180 g of 5% platinum on carbon and 3 L of water were charged into a 4-L glass reactor equipped with a thermometer and a reflux condenser. As the mixture was refluxed at 60° C. with agitation, a reaction was performed for 24 h under bubbling with oxygen. After the end of the reaction, the reaction mixture was neutralized with sodium bicarbonate and filtered to remove the platinum on carbon; thereafter, the solvent was distilled off under vacuum to give 315 g of a pale yellow powder. Analysis by high-performance liquid chromatography revealed that the product contained α-D-glucuronyl-α-D-glucuronic acid sodium salt (oxidized trehalose) in a yield of 96.0% relative to the starting trehalose.

Example 1-2: Production of D-glucuronolactone from Oxidized Trehalose

A portion (1.48 g, 3.57 mmol) of the oxidized trehalose prepared in Example 1-1 and 20 ml of water were charged into a 50-ml glass reactor equipped with a thermometer and a reflux condenser. After addition of 1.18 g (11.6 mmol) of conc, sulfuric acid, the mixture was refluxed at 80° C. with agitation while the reaction progressed for 6 h. After the end of the reaction, the insolubles in the reaction mixture were filtered off and the filtrate was deionized using a column packed with an ion-exchange resin. The solvent was distilled off under vacuum to yield 518 mg of a white crystal. Analysis by high-performance liquid chromatography showed that the product contained 2.91 mmol of D-glucuronolactone in a yield of 35.0% relative to the starting trehalose.

Example 2: Production of D-glucuronolactone

Example 2-1: Preparation of Oxidized Trehalose

Five grams (13.2 mmol) of α,β-trehalose, 1.0 g of platinum oxide and 100 ml of water were charged into a 200-ml glass reactor equipped with a thermometer and a reflux condenser. As the mixture was refluxed at 60° C. with agitation, a reaction was performed for 24 h under bubbling with oxygen. After the end of the reaction, the reaction mixture was neutralized with sodium bicarbonate and filtered to remove the platinum oxide; thereafter, the solvent was distilled off under vacuum to give 5.22 g of a pale yellow powder. Analysis by high-performance liquid chromatography revealed that the product contained α-D-glucuronyl-β-D-glucuronic acid sodium salt (oxidized trehalose) in a yield of 95.5% relative to the starting trehalose.

Example 2-2: Production of D-glucuronolactone from Oxidized Trehalose

A portion (1.48 g, 3.57 mmol) of the oxidized trehalose prepared in Example 2-1 and 20 ml of water were charged into a 50-ml glass reactor equipped with a thermometer and a reflux condenser. After addition of 2.64 g (2.69 mmol) of cone. hydrochloric acid, the mixture was refluxed at 100° C. with agitation while the reaction progressed for 6 h. After the and of the reaction, the insolubles in the reaction mixture were filtered off and the filtrate was deionized using a column packed with an ion-exchange resin. The solvent was distilled off under vacuum to yield 548 mg of a white crystal. Analysis by high-performance liquid chromatography showed that the product contained 3.08 mmol of D-glucuronolactone in a yield of 37.0% relative to the starting trehalose.

Example 3: Production of D-glucuronolactone

Example 3-1: Preparation of Oxidized Trehalose

A specified amount (4.99 g, 13.2 mmol) of β, β-trehalose, 3.0 g of 5% platinum on carbon and 100 ml of water were charged into a 200-ml glass reactor equipped with a thermometer and a reflux condenser. As the mixture was refluxed at 70° C. with agitation, a reaction was performed for 24 h under bubbling with air. After the end of the reaction, the reaction mixture was neutralized with sodium bicarbonate and filtered to remove the platinum on carbon; thereafter, the solvent was distilled off under vacuum to give 5.29 g of a pale yellow powder. Analysis by high-performance chromatography revealed that the product contained β-D-glucuronyl-β-D-glucuronic acid sodium salt (oxidized trehalose) in a yield of 97.5% relative to the starting trehalose.

Example 3-2: Production of D-glucuronolactone from Oxidized Trehalose

A portion (1.48 g, 3.57 mmol) of the oxidized trehalose prepared in Example 3-1 and 20 ml of water were charged into a 50-ml glass reactor equipped with a thermometer and are a reflux condenser. After addition of 2.64 g (2.69 mmol) of conc. hydrochloric acid, the mixture was refluxed at 100° C. with agitation while the reaction progressed for 6 h. After the end of the reaction, the insolubles in the reaction mixture were filtered off and the filtrate was deionized using a column packed with an ion-exchange resin. The solvent was distilled off under vacuum to yield 548 mg of a white crystal. Analysis by high-performance liquid chromatography showed that the product contained 3.08 mmol of D-glucuronolactone in a yield of 37.0% relative to the starting trehalose.

Example 4: Production of D-glucuronolactone

Example 4-1: Preparation of Oxidized Trehalose

Hydrous crystals of high-purity α, α-trehalose (2.50 g, 6.6 mmol), vanadium oxide (0.5 g) and ethanol (50 ml) were charged into a 100-ml glass reactor equipped with a thermometer and a reflux condenser. As the mixture was refluxed at 40° C. with agitation, a reaction was performed for 48 h under bubbling with air. After the end of the reaction, the reaction mixture was neutralized with sodium bicarbonate and filtered to remove the vanadium oxide; thereafter, the solvent was distilled off under vacuum to give 2.61 g of a pale yellow powder. Analysis by high-performance chromatography revealed that the product contained α-D-glucuronyl-α-D-glucuronic acid sodium salt (oxidized trehalose) in a yield of 97.0% relative to the starting trehalose.

Example 4-2: Production of D-glucuronolactone from Oxidized Trehalose

A portion (1.48 g. 3.57 mmol) of the oxidized trehalose prepared in Example 4-1 and 20 ml of water were charged into a 50-ml glass reactor equipped with a thermometer and a reflux condenser. After addition of 2.64 g (2.69 mmol) of conc. hydrochloric acid, the mixture was refluxed at 90° C. with agitation while the reaction progressed for 10 h. After the end of the reaction, the insolubles in the reaction mixture were filtered off and the filtrate was deionized using a column packed with an ion-exchange resin. The solvent was distilled off under vacuum to yield 603 mg of a white crystal. Analysis by high-performance chromatography showed that the product contained 3.39 mmol of D-glucuronolactone in a yield of 44.0% relative to the starting trehalose.

INDUSTRIAL APPLICABILITY

As described on the foregoing pages, the present invention not only improves the yield of D=glucuronolactone; it also eliminates foaming from the process of production of D-glucuronolactone and, hence the throughput of D-glucuronolactone per batch is remarkably increased to achieve a significant improvement in reactor's efficiency. Therefore, one may well say that the process of the invention for producing D-glucuronolactone is an industrially superior approach that features a by far higher efficiency in the production of D-glucuronolactone than the currently practiced processes.

What is claimed is:

1. A process for producing D-glucuronolactone comprising the steps of oxidizing trehalose, then hydrolyzing the oxidized trehalose to form D-glucuronolactone and recovering the same.

2. The process according to claim 1, wherein the trehalose is prepared by allowing an enzyme to act on a partial hydrolyzate of starch and/or maltose.

3. The process according to claim 1, wherein the trehalose is anhydrous or hydrous trehalose.

4. The process according to claim 1, wherein the trehalose is crystalline or noncrystalline.

5. The process according to claim 1, wherein the trehalose is oxidized either with one or more oxidizers selected from among inorganic nitrogen compounds, inorganic metal compounds, halogens, inorganic halogen compounds, oxygen species, inorganic peroxides and organic compounds or by electro-oxidation or oxidative fermentation.

6. The process according to claim 1, wherein the trehalose is oxidized under a superatmospheric pressure condition.

7. The process according to claim 1, wherein the trehalose is oxidized in the presence of one or more oxidation catalysts selected from among platinum oxide, platinum on carbon, vanadium oxide and palladium on carbon.

8. The process according to claim 1, wherein the oxidized trehalose is hydrolyzed using one or more hydrolyzing agents selected from among hydrochloric acid, sulfuric acid, nitric acid, phosphoric acid, tosic acid and enzymes.

9. The process according to claim 2, wherein the trehalose is oxidized either with one or more oxidizers selected from among inorganic nitrogen compounds, inorganic metal compound, halogens, inorganic halogen compounds, oxygen species, inorganic peroxides and organic compounds or by electro-oxidation or oxidative fermentation.

10. The process according to claim 2, wherein the trehalose is oxidized under a superatmospheric pressure condition.

11. The process according to claim 2, wherein the trehalose is oxidized in the presence of one or more oxidation catalysts selected from among platinum oxide, platinum on carbon, vanadium oxide and palladium on carbon.

12. The process according to claim 2, wherein the oxidized trehalose is hydrolyzed using one or more hydrolyzing agents selected from among hydrochloric acid, sulfuric acid, nitric acid, phosphoric acid, tosic acid and enzymes.

13. The process according to claim 5, wherein the trehalose is oxidized under a superatmospheric pressure condition.

14. The process according to claim 5, wherein the trehalose is oxidized in the presence of one or more oxidation catalysts selected from among platinum oxide, platinum on carbon, vanadium oxide and palladium on carbon.

15. The process according to claim 5, wherein the oxidized trehalose is hydrolyzed using one or more hydrolyzing agents selected from among hydrochloric acid, sulfuric acid, nitric acid, phosphoric acid, tosic acid and enzymes.

16. The process according to claim 6, wherein the trehalose is oxidized in the presence of one or more oxidation catalysts selected from among platinum oxide, platinum on carbon, vanadium oxide and palladium on carbon.

17. The process according to claim 6, wherein the oxidized trehalose is hydrolyzed using one or more hydrolyzing agents selected from among hydrochloric acid, sulfuric acid, nitric acid, phosphoric acid, tosic acid and enzymes.

18. The process according to claim 7, wherein the oxidized trehalose is hydrolyzed using one or more hydrolyzing agents selected from among hydrochloric acid, sulfuric acid, nitric acid, phosphoric acid, tosic acid and enzymes.

* * * * *